| United States Patent [19] | [11] Patent Number: 4,508,930 |
| --- | --- |
| Wideman et al. | [45] Date of Patent: Apr. 2, 1985 |

[54] PROCESS FOR THE CONVERSION OF TERPENES TO LIMONENE

[75] Inventors: Lawson G. Wideman, Tallmadge; Lynn A. Bente, Dover, both of Ohio

[73] Assignee: The Goodyear Tire & Rubber Company, Akron, Ohio

[21] Appl. No.: 632,746

[22] Filed: Jul. 20, 1984

[51] Int. Cl.³ .................. C07C 5/24; C07C 5/26
[52] U.S. Cl. .................. 585/377; 585/378; 585/947; 585/364; 585/371
[58] Field of Search ......... 585/364, 371, 374, 375, 585/377, 378, 643, 671, 947; 502/216

[56] References Cited

U.S. PATENT DOCUMENTS

| 3,399,244 | 8/1968 | Gut et al. | 585/378 |
| 3,407,241 | 10/1968 | Booth | 585/378 |
| 3,700,747 | 10/1972 | Takacs | 585/377 |
| 3,819,737 | 6/1974 | Kubitz et al. | 585/947 |
| 3,974,103 | 8/1976 | Kaiser | 585/947 |

FOREIGN PATENT DOCUMENTS

| 2744386 | 3/1977 | Fed. Rep. of Germany | 585/377 |
| 0606851 | 5/1978 | U.S.S.R. | 585/947 |

OTHER PUBLICATIONS

Gassman et al, J. Am. Chem. Soc., (1983), vol. 103, pp. 667–669.

*Primary Examiner*—Delbert E. Gantz
*Assistant Examiner*—A. Pal
*Attorney, Agent, or Firm*—M. R. Dion

[57] ABSTRACT

There is disclosed a process for the conversion of terpenes to limonene which comprises contacting at least one terpene, selected from the group comprised of mono- and bi-cyclic unsaturated hydrocarbons having the formula $C_{10}H_{16}$ with an alkali metal sulfide catalyst on a support at a temperature of 300° to 450° C.

16 Claims, No Drawings

PROCESS FOR THE CONVERSION OF TERPENES TO LIMONENE

TECHNICAL FIELD

This invention is concerned with the economic conversion of terpenes to limonene. More specifically, this invention is concerned with a process to convert a renewable hydrocarbon source, that being the volatile oil present in trees, to a compound that can provide an alternative source of hydrocarbon feed stocks that are non-petroleum based. The process of the present invention accomplishes the conversion of terpenes to limonene by contacting at least one terpene, which is a mono- or bi-cyclic unsaturated hydrocarbon having the formula $C_{10}H_{16}$, with an alkali metal sulfide catalyst on a carrier at a temperature of 300° to 450° C.

BACKGROUND ART

Turpentine is the general term for the volatile oil present in trees, primarily coniferous trees. Chemically, it is predominately a mixture of unsaturated mono- and bi-cyclic $C_{10}H_{16}$ terpenes. The principal component is alpha-pinene, which is present in the turpentine from all species of turpentine bearing trees.

The composition of the turpentine is determined by the species of the tree. A chromatograph of the turpentine makes a good fingerprint for identifying the species.

Although over thirty compounds have been identified in turpentine only a few have commercial significance, that is, they can be separated in high purity for subsequent use. Alpha-pinene, beta-pinene, and beta-phellandrene and dipentene are present in large enough volume in gum or sulfate turpentines of most species to make isolation feasible. Δ-3 carene is present in large quantities in certain species, especially in the northwestern and Scandinavian pines. The terpenes undergo numerous reactions including hydrogenation, isomerization, polymerization, oxidation, halogenation, esterification and dehydrogenation.

There has been and continues to this day investigations concerning the production of high volume chemicals from nonpetroleum base sources. Trees, especially coniferous trees, are a renewable resource that can be ground into wood chips and have extracted therefrom resins and terpenes. Terpenes are therefore a renewable resource that may be used to replace the present petroleum base source of most of industry's hydrocarbons. However, a turpentine or a mixture of terpenes, in and of itself, is not a commercially significant hydrocarbon feed stock. Therefore, a process that will readily convert a terpene or a turpentine feed stock into a valuable or commercially more acceptable compound is highly desirable.

In the past numerous publications have reported the conversion of turpentine to various chemical compounds using numerous reaction conditions and catalysts. More specifically, U.S. Pat. Nos. 3,780,124; 3,780,125; 3,700,746; 3,700,747, and 3,642,928 all disclose the use of zeolites to isomerize terpenes to limonene. In U.S. Pat. Nos. 3,359,342 and 3,360,581, Derfer discloses the need to pretreat α-pinene streams containing catalyst poisons with a Group VIII metal in the presence of hydrogen or with metallic sodium in order to prevent poisoning of the isomerization catalysts. However, none of the prior art publications disclose or suggest the process for the conversion of terpenes to limonene which comprises contacting at least one terpene selected from the group consisting of mono- and bi-cyclic unsaturated hydrocarbons having the formul $C_{10}H_{16}$ with an alkali metal sulfide catalyst on a carrier at a temperature of 300° to 450° C. at a LHSV of 0.20 to 20.

DISCLOSURE OF THE INVENTION

There is disclosed a process for the conversion of terpenes to limonene which comprises contacting at least one terpene, selected from the group comprised of mono- and bi-cyclic unsaturated hydrocarbons having the formula $C_{10}H_{16}$ with an alkali metal sulfide catalyst on a support at a temperature of 300° to 450° C.

Terpenes in the strict sense are volatile hydrocarbons of the empirical formula $C_{10}H_{16}$. In a wider sense the term includes sesquiterpenes, $C_{15}H_{24}$, diterpenes, $C_{20}H_{32}$, and higher polymers. In a still wider sense, the term includes various oxygen containing compounds derived from terpene hydrocarbons, such as alcohols, ketones and camphors. The terpenes are based on the isoprene unit, $C_5H_8$, and may be either acyclic or cyclic. Representative of the terpenes that can be used in the process of the present invention are alpha-pinene, beta-pinene, Δ-3 carene and terpinolene.

The conversion of terpenes to limonene is of significant importance since it could provide a renewable hydrocarbon source for conversion of limonene to isoprene. Isoprene is the conjugated monomer which may be polymerized into polyisoprene, a synthetic version of natural rubber.

Representative of the alkali metal sulfide catalysts that are useful in the process of this invention are sodium sulfide, lithium sulfide, and potassium sulfide or mixtures thereof. The alkali metal sulfides may be in the anhydrous or hydrated forms. The hydrated forms lose their water of hydration at the temperatures employed in the reaction. The process of the present invention is conducted using the alkali metal sulfide supported on a carrier. Supporting the alkali metal sulfide on a carrier is required since this provides a greater surface area of catalyst per gram of material. Representative of the carriers upon which the alkali metal sulfides can be supported are silica; aluminum oxide ($Al_2O_3$); magnesium oxide (MgO); carbon (C) and titanium dioxide ($TiO_2$). However, any carrier that does not detrimentally effect the activity of the alkali metal sulfide and has a surface area of at least 5 m²/gm may be used. To ensure a good efficiency of the catalyst the specific surface area of the carrier material should generally be larger than 5 m²/gm and preferably larger than 10 m²/gm. Aluminum oxide and magnesium oxide are the preferred carriers for the alkali metal sulfides.

The catalyst system should contain from 5–30 weight percent of the alkali metal sulfide based on the total catalyst plus carrier. Preferably, the catalyst system contains from 10–25 weight percent of the alkali metal sulfide.

The amount of catalyst used is related to the LHSV of the reaction system. The LHSV, liquid hourly space velocity, is the hourly volume of liquid throughput per gross volume of catalyst. A gross volume of catalyst is the actual volume plus the interstitial volume. For example, 90 ml of liquid feed is passed over 45 cc (gross volume) of catalyst in one hour to yield an LHSV of 2. See *Chem. Eng. Kinetics*, J. M. Smith, McGraw-Hill, N.Y., pp 99–100 (1956). A LHSV should be large enough, above 0.20, so as to effect efficient conversion of terpenes to limonene, but not so large, below 20, as to effect the selectivity.

The manufacturing methods for catalysts containing alkali metals on aluminum oxide have been well known for years and are disclosed in numerous publications and also in numerous patents, such as U.S. Pat. No. 2,836,633. In a preferred embodiment, the catalyst of this invention is prepared by dissolving the alkali metal sulfide in water and pouring it over the carrier material followed by drying under a protective atmosphere of nitrogen to prevent oxidation. After it is manufactured, the catalyst may be in the form of granules, powder, pellets or extrudates.

The temperature at which the process of the present invention can be conducted ranges from 300° to 450° C. A more preferred temperature range is from 350° to 425° C.

The process of the present invention may be carried out either batchwise or continuously. However, due to numerous operating difficulties and poor yields which result from batchwise operation, a continuous process is preferred. The process is carried out in the vapor phase due to the temperature being greater than the boiling point of the reactants. The process is carried out in the presence of an inert atmosphere to preclude the formation of peroxides should oxygen be present. The process may be carried out at atmospheric pressure or at superatmospheric pressure.

BEST MODE FOR CARRYING OUT THE INVENTION

The process of the present invention is preferably carried out in a tubular reactor in an upflow or downflow manner. A preheater is used to vaporize the terpenes prior to passage through the reactor. Proper temperature control of the catalyst bed and reaction wall temperatures is required to achieve satisfactory results. A flow of an inert gas, about 1% by weight based on the terpene feed, for example nitrogen or carbon dioxide, is used as the carrier gas in the reactor. The reactor catalyst bed and the preheater are all brought up to the reaction temperature prior to introduction of the terpene stream. The terpene feed stream is volatized in the preheater and then is carried by the inert gas to the reactor which contains the catalyst bed. The LHSV of the terpene feed over the catalyst bed may range from 0.20 to 20 with a rate of 0.4 to 20 being more preferred and a rate of 0.4 to 10 being the most preferred.

CATALYST PREPARATION

The catalyst was prepared as follows. Twenty-one grams of hydrated sodium sulfide were dissolved in 40 ml of water and poured over 57 g. of a commercially available aluminum oxide having a surface area of 10 m²/g. The water was removed by heating to 100° C. under a stream of nitrogen to prevent oxidation of the catalyst.

EXAMPLE 1

A 10 inch by three-quarter inch tubular stainless steel reactor was charged with 45 cc of the sodium sulfide catalyst prepared above. A constant flow of 7 ml/min of nitrogen was used to protect the catalyst from oxidation. Two feed stocks were run. The first was a turpentine (Runs 1, 2, 3, 7, and 8) in which an analysis indicated was 57.7% α-pinene, 40.7% β-pinene and 1.5% limonene. The other was a neat α-pinene stream (Runs 4, 5, and 6). Both feeds contained an added 12% heptane as an internal gas chromatographic standard. The feed was metered into the tubular reactor in a downflow manner. A glass bead preheater was used to vaporize the feed prior to contact with the catalyst. The reactor was fitted with a heating jacket with manual temperature controls and a catalyst bed thermocouple array to monitor the internal temperature. The reactions were carried out at atmospheric pressure.

The tubular reactor and preheater were heated to the desired reaction temperature before introduction of the feed. The effluent stream from the reactor was condensed in a dry ice-acetone bath prior to gas chromatograph and NMR analysis. The sensitivity of the feed streams and limonene to the GC detector had been predetermined. The samples were collected after one hour on stream. The percent feed stream conversion and percent selectivity to limonene are shown in Table I along with the conditions of temperature and LHSV.

$$\text{Percent Conversion} = \frac{A - B}{A} \times 100$$

where
A = weight ratio of terpenes in the feed.
B = weight ratio of terpenes in the product.

$$\text{Percent Selectivity to limonene} = \frac{C}{A - B} \times 100$$

where
C = weight ratio limonene in the product.
A = weight ratio of terpenes in the feed.
B = weight ratio of terpenes in the product.

EXAMPLE 2

A "sulfate" turpentine from the Kraft paper pulp industry, containing 600 ppm sulfides, is fed to the reactor as described in Example 1. The LHSV is 1.3 and temperature is controlled at 350° C. The percent conversion and % selectivity to limonene is expected to be similar to Run 8 of Example 1 since the alkali metal sulfide catalyst is not expected to be affected by the presence of sulfides.

TABLE I

| Run | Feed | Reactor Temperature 20° C. | Feed LHSV | % Conversion | Limonene Selectivity |
|---|---|---|---|---|---|
| 1 | Turpentine | 350 | 0.24 | 90 | 34 |
| 2 | Turpentine | 400 | 0.24 | 92 | 33 |
| 3 | Turpentine | 450 | 0.24 | 100 | 23 |
| 4 | α-pinene | 350 | 0.48 | 85 | 36 |
| 5 | α-pinene | 400 | 0.48 | 88 | 35 |
| 6 | α-pinene | 450 | 0.48 | 95 | 26 |
| 7 | Turpentine | 250 | 1.3 | 0 | 0 |
| 8 | Turpentine | 350 | 1.3 | 44 | 90 |

INDUSTRIAL APPLICABILITY

The process of the present invention provides a means for the conversion of a renewable feed stock, turpentine, to a compound that is significantly more important as a commercial feed stock. In addition, the process of the present invention accomplishes this conversion without the use of expensive and sometimes easily poisoned catalysts, such as platinum on carbon, and does so in an efficient and selective manner. Thus, the process of the present invention provides a viable and economic means for the conversion of a renewable hydrocarbon feed stock into a more commercially acceptable aromatic feed stock.

The present invention employs a sulfur-containing catalyst that is believed to not be poisoned by the presence of sulfur or sulfur-containing impurities, such as sulfides, mercaptans, or sulfates in the turpentine stream which can be present at levels from 1 to 1000 ppm. This tolerance for sulfur containing compounds in the turpentine stream is especially important for utilizing "Sulfate" turpentine from the high-volume Kraft paper pulp industry.

While certain representative embodiments and details have been shown for the purpose of illustrating the invention, it will be apparent to those skilled in this art that various changes and modifications may be made therein without departing from the scope of the invention.

What is claimed is:

1. A process for the conversion of a terpene to limonene which comprises contacting at least one terpene selected from the group consisting of mono- and bicyclic unsaturated hydrocarbons having the formula $C_{10}H_{16}$, with an alkali metal sulfide catalyst on a carrier at a temperature from 300° C. to 450° C.

2. A process according to claim 1 wherein the terpene is selected from the group consisting of α-pinene, β-pinene, terpinolene, and Δ-3 carene.

3. A process according to claim 1 wherein the alkali metal sulfide is selected from the group consisting of $Na_2S$, $Li_2S$ and $K_2S$.

4. A process according to claim 1 wherein the temperature of the reaction is from 350° C. to 450° C.

5. A process according to claim 1 wherein the alkali metal sulfide is sodium sulfide and the carrier is aluminum oxide.

6. A process according to claim 1 wherein the terpene stream is fed at a liquid hourly space velocity (LHSV) of 0.20 to 20.

7. A process according to claim 6 wherein the alkali metal sulfide is selected from the group consisting of $Na_2S$, $Li_2S$ and $K_2S$.

8. A process according to claim 6 wherein the temperature of the reaction is from 350° C. to 450° C.

9. A process according to claim 6 wherein the alkali metal sulfide is sodium sulfide.

10. A process according to claim 9 wherein the temperature of the reaction is 350° C. to 450° C., the carrier is aluminum oxide and the LHSV is 0.24 to 10.

11. A process according to claim 10 wherein the terpene stream is in the form of a sulfate turpentine.

12. A process according to claim 11 wherein the sulfate turpentine contains sulfur or sulfur containing impurities at levels from 1 ppm to 1000 ppm.

13. A process according to claim 6 wherein the reaction is carried out in an inert atmosphere.

14. A process according to claim 13 wherein the inert atmosphere is nitrogen.

15. A process according to claim 6 wherein the catalyst is comprised of 5 to 30 percent by weight based on the total catalyst plus carrier.

16. A process according to claim 1 wherein the terpene feed is vaporized prior to contacting the catalyst bed, wherein the catalyst bed is preheated to the reaction temperature, wherein an inert carrier gas is used and wherein the terpene feed stream is fed at a LHSV of from 0.20 to 20.

* * * * *